(12) United States Patent
Aberle et al.

(10) Patent No.: US 6,873,412 B2
(45) Date of Patent: Mar. 29, 2005

(54) METHOD AND DEVICE FOR SUPPRESSING MULTIPLE SCATTERING WHEN EXAMINING TURBID MEDIA BY MEANS OF THREE-DIMENSIONAL CROSS-CORRELATION TECHNIQUE

(75) Inventors: Lisa Birgit Aberle, Bremen (DE); Wilfried Straude, Bremen (DE); Malte Kleemeier, Bremen (DE); Jürgen Loschen, Oldenburg (DE)

(73) Assignee: Fraunhofer Gesellschaft zur Forderung der Angewandten Forschung e.V., München (DE)

( * ) Notice: Subject to any disclaimer, the term of this patent is extended or adjusted under 35 U.S.C. 154(b) by 0 days.

(21) Appl. No.: 10/301,002

(22) Filed: Nov. 21, 2002

(65) Prior Publication Data
US 2003/0128363 A1 Jul. 10, 2003

Related U.S. Application Data

(63) Continuation of application No. PCT/DE01/02005, filed on May 25, 2001.

(30) Foreign Application Priority Data

| May 25, 2000 | (DE) | ......................................... 100 25 758 |
| Sep. 25, 2000 | (DE) | ......................................... 100 47 340 |
| Sep. 25, 2000 | (DE) | ......................................... 100 47 339 |
| Dec. 4, 2000 | (DE) | ......................................... 100 60 200 |
| Apr. 2, 2001 | (DE) | ......................................... 100 16 383 |

(51) Int. Cl.$^7$ .............................................. G01N 15/02
(52) U.S. Cl. ........................ 356/336; 356/441; 250/574; 73/53.01
(58) Field of Search ............................... 356/335–336, 356/337–343, 441; 250/573, 574; 73/53.01–64.56, 64.66

(56) References Cited

U.S. PATENT DOCUMENTS 4,329,054 A   5/1982   Bachalo ...................... 356/336

(List continued on next page.)

FOREIGN PATENT DOCUMENTS

| DE | 197 55 589 | 8/1999 |
| EP | 0 872 722 | 10/1998 |
| EP | 0 899 548 | 3/1999 |

OTHER PUBLICATIONS

Aberle, et al., Effective Suppression of Multiply Scattered Light in Static and Dynamic Light Scattering, Applied Optics, vol. 37 No. 27, Sep. 20, 1998, pp. 6511–6523.*

(List continued on next page.)

*Primary Examiner*—Richard A. Rosenberger
*Assistant Examiner*—Vincent P. Barth
(74) *Attorney, Agent, or Firm*—Schnader Harrison Segal & Lewis LLP

(57) ABSTRACT

The invention relates to a portable device for carrying out examinations of turbid media using a three-dimensional cross-correlation technique and for suppressing the influence of multiple scattering, as well as to an adjustment method for adjusting the device. The device has a base plate (1) upon which an adjustable laser (2) is positioned in tilting devices or by means of mirrors for directing the laser beam perpendicularly onto the wall of a cuvette (6) filled with a medium to be examined. The device is provided with a translucent plate (7) which in some sections is completely mirror-coated and in other sections is partially mirror-coated and which serves as a beam splitter (4). The plate is firmly secured to the base plate (1) using a positioning fixture (8) whose support surface (16) for the translucent plate (7) is situated at a fixed angle with respect to the base plate (1). The positioning fixture (8) is detachably secured to the base plate (1) and to a cuvette fixture having receptacles for the cuvette (6) and for a cylindrical translucent container (70) filled with a liquid which is situated on the base plate (1). Displacement devices for the cuvette fixture (5) which allow the cuvette to be continuously positioned are also mounted on the base plate. Tilting and displacement devices for at least two detection optics are situated so that they can be fixedly positioned on a base plate on the detection side of the device and so that this base plate can be firmly locked on the base plate (1). Photon multipliers and correlators for receiving cross-correlation or auto-correlation functions are also provided.

46 Claims, 24 Drawing Sheets

U.S. PATENT DOCUMENTS 4,701,051 A    10/1987    Buchhave et al. .......... 356/336

OTHER PUBLICATIONS

PCT International Search Report.

Aberle, L. B., et al. Suppression of Multiple Scattered Light by Photon Cross–Correlation in a 3D Experiment, *Progr. Colloid Polym Sci.*, 104:121–125 (1997).

* cited by examiner

METHOD AND DEVICE FOR SUPPRESSING MULTIPLE SCATTERING WHEN EXAMINING TURBID MEDIA BY MEANS OF THREE-DIMENSIONAL CROSS-CORRELATION TECHNIQUE

This is a continuation of Application No. PCT/DE01/02005, filed on May 25, 2001.

The invention relates to a method and a device for suppressing multiple scattering when examining turbid media using a three-dimensional cross-correlation technique according to the preamble of Claims 1 and 24.

For many years, light scattering techniques have ranked among the established methods for characterizing liquid samples, such as for example the determination of particle size distribution and molar mass, dynamic processes, and structural properties of suspensions, emulsions, and polymer solutions. However, conventional light scattering techniques have always had the disadvantage that only highly diluted or almost transparent samples can be analyzed, and that turbid samples are not amenable to this technique because of problems associated with multiple scattering. Cross-correlation techniques are special light scattering techniques that have been developed to suppress the influence of multiple scattering and to select singly scattered light. These techniques thus allow the examination of media over a wide concentration range, from nearly transparent to highly opaque. Even samples that are so turbid that the proportion of singly scattered light is only a few percent can be examined.

Devices and methods for three-dimensional cross-correlation techniques for angle-dependent measurements are known. The adjustment of three-dimensional cross-correlation analyses and devices is considerably more difficult compared to conventional DLS analyses. Such structures naturally contain many components which are sensitive to shocks and vibrations and which therefore are not suited for industrial use or for routine examinations. In addition, angle-dependent light scattering equipment is costly, and it is time-consuming to operate on account of the extensive adjustment procedure. Although the apparatus proposed by Aberle et al., Progr. Collid. Polym. Sci. 104, 121 (1997), is designed only for a fixed scattering angle of 90°, the apparatus is likewise time-consuming to adjust and contains components that are similarly sensitive to shocks. The adjustment of a three-dimensional cross-correlation apparatus is sensitive to disturbance by the slightest shock, so that the apparatus sends poor signals, or none at all.

German Patent Application 197 55 589 A1 also describes an adjustment procedure for variable scattering angle adjustment and a device for carrying out tests on turbid media using a cross-correlation technique. Use is made of the fact that the "copying process" for the geometric conditions of the laser beams illuminating the sample is then carried out by adjusting the scattering angle θ to 0° for the detection optics. Before this step can be performed, however, the entire apparatus must be pre-adjusted with respect to the correct angle adjustment. In other words, the rotation point of the goniometer is aligned with the incident laser beams, the midpoints of the temperature-controlling bath and sample cuvettes are aligned with the rotation point of the goniometer, the longitudinal axis of the temperature-controlling bath is aligned with the optical plane, and so forth. This adjustment is complicated and requires highly technical knowledge on the part of the operator. In addition, the described device is suited only for stationary use, since it requires much space and is sensitive to the slightest shocks.

The object of the present invention is to provide an adjustment method that is easily carried out, and to provide a device that is user-friendly and inexpensive.

This object is achieved by the characterizing features of Claims 1 and 24.

The subclaims represent advantageous developments.

In three-dimensional cross-correlation analyses, small adjustment errors or maladjustment effects easily result in the total inability to measure a cross-correlation signal. Consequently, the adjustment alone places great demands on the precision and stability. Since the scattering geometries specified by the directions of incidence of the laser beams and the directions of detection are present in three-dimensional space, refraction effects appear at transitions between air, cuvette material, and sample liquid which must be taken into account during the adjustment. It is therefore important to ensure that the conditions which will later be present during the measurement process already exist during the adjustment.

The two laser beams which illuminate the medium present in a test container must have maximum optimal crossover in the medium. To this end, two parallel beams are produced which are then inclined so that their point of intersection is situated in the test container. The higher the quality of parallelism of the two beams, the better the crossover between the beams, which can be achieved by using a lens, for example. When parallelism is insufficient, the laser beams either do not intersect at all, or intersect only in a small volume of the medium to be examined. If at the beginning of the adjustment there is insufficient or no intersection of the two laser beams, one of the prerequisites for measuring cross-correlation functions is already not being met. Even if further adjustment should be carried out with high precision, it would not be possible to measure the cross-correlation function. In addition, during the next successful adjustment, if subsequent shocks or other factors (transport, operation) disturb the parallelism of the laser beams, no further measurement of the cross-correlation signal can likewise be performed. The two detection optics must also be adjusted in such a way that they detect scattered light from the same sample volume, also known as the overlap volume. This overlap volume must have the greatest possible congruency with the volume of the medium in which the two laser beams intersect. Here as well, no cross-correlation function can be measured if there is no common volume from which scattering light reaches the detection optics.

The adjustment method is carried out as follows:

In the first step, the laser beam is adjusted so that, according to one advantageous embodiment of the invention, it perpendicularly strikes the wall of the test container of a cuvette filled with a liquid. It was found that the determining factor was not the parallel alignment of the laser beam with the optical plane, but rather the perpendicular alignment of the laser beam with respect to the wall of the test container, or in other words, the positioning of the laser beam relative to the cuvette. To this end, the laser is adjusted using tilting devices and/or mirrors so that the laser beam perpendicularly strikes the wall of the cuvette present in a cuvette fixture. For this purpose, the embodiment of the method provides for the use of a cuvette which produces the maximum optimal reflection of the incident laser light on the cuvette wall. This is achieved by placing a dark or black liquid in the cuvette. Together with the cuvette material (glass or plastic), the black/dark liquid acts as a mirror. The use of a mirror-coated cuvette or a reflecting metal block having the dimensions of the cuvette is also suitable. The positions of the reflected light and of the light emitted from the laser are then observed using a thin glass plate which is placed at the greatest possible distance from the reflecting cuvette, but in the beam path between this cuvette and the laser. In this manner the accuracy of adjustment is improved. In addition, the adjustment is independent of the base plate of the device which forms the optical plane. This is advantageous for the production of the individual components for the cuvette fixture. The adjustment of the perpendicular incidence of the laser beam on a wall of the test container is carried out as follows: The laser beam emitted from the laser is tilted, using tilting devices or mirrors, so that the laser beam reflected on the cuvette wall returns back to the laser beam emitted from the laser. This may be easily observed using a glass plate placed in the beam path. The point of impact of the reflected laser beam and the laser beam emitted from the laser creates bright spots of light when the beams strike the glass plate. The laser beam emitted from the laser is adjusted in such a way that these two spots of light become superimposed. In one advantageous embodiment of the method, the laser beam is first adjusted so that it intersects a centerline marked on the cuvette corresponding to the central axis of the cuvette. This centerline is a line which runs parallel to the longitudinal edges of the cuvette and which is equidistant from these longitudinal edges. The laser beam is then vertically displaced with respect to this centerline so as to intersect the centerline.

The second step of the method involves the creation of the conditions that the "copying process", which is to be subsequently performed, proceeds with maximum accuracy. The laser beam is split into two parallel beams. The parallel beams are then inclined so that their point of intersection is situated inside the cuvette. Care is taken that, on account of the inclination of the incident laser beams, these laser beams are refracted during the transitions from air to glass (or air to plastic) and glass (or plastic) to the medium that is to be examined. Only in this manner is assurance provided that the overlap volume of the detection optics is congruent with the intersection volume of the laser beams after the adjustment is completed, even in the actual experiment. In the measurements it is critical that the intersection point of the laser beams is situated at the location of the overlap volume of the detection optics during the subsequent measurements, that is, at the location where a mirror surface is present in the next step of the method. The mirror surface advantageously contains the central axis of the test container. If the point of intersection were situated in front of or behind this mirror surface, this would result in the two detection optics, according to the "copying process," receiving scattered light from an overlap volume situated behind or in front of the point of intersection of the laser beams.

The parallel laser beams may be focused using a lens placed in the beam path of the laser beams. For this step of the method, the mirror-coated cuvette is replaced by a new cuvette. The point of intersection of the two laser beams may then be observed particularly well in an advantageous manner if a slightly turbid liquid, with a refractive index matching as closely as possible that of the media that is to be subsequently examined, is placed in the cuvette. The course of the laser beams is imaged through scattering effects in the slightly turbid liquid. The markings on the cuvette indicate the center of the cuvette, and the intersecting laser beams are easily observed along with the markings, using a magnifying lens. Because the parallel laser beams intersect in the focal point of the lens, the position of the lens as well may be easily determined quite accurately. Alternatively, this step of the method may be carried out in such a way that the laser beam is first focused through a lens, and this focused laser beam is then split into two laser beams that are directed so that they intersect inside the cuvette, advantageously on the central axis of the cuvette. This arrangement has the advantage that a lens having a longer focal length may be used, resulting in an enlarged diameter of the overlap region. The same is true if the lens is omitted altogether and in its place a specially designed prism is used which splits the laser beam into two beams and inclines the beams so that the point of intersection is situated in the overlap volume, as desired.

In the third step of the method a diagonal mirror surface is provided in a cuvette. In one advantageous embodiment of the invention, the mirror surface contains the central axis of the cuvette, and thus the central axis of the cuvette fixture as well. A liquid is present in the cuvette whose refractive index is as close as possible to the value of the refractive index of the media to be examined, as a result of which, according to the copying process, also the overlap volume of the detection optics comprises the largest possible volume in which the laser beams intersect.

In the fourth step of the method the reflected laser light is admitted by the detection optics. The cuvette having the mirror surface is then replaced by a cuvette having a weakly scattering liquid, and the amplitude of the cross-correlation functions is optimized according to known methods. The coupling of the reflecting laser light in the glass fibers is improved due to the fact that the beams are not impaired by the refraction effect of a liquid which is present in a cylindrical container and which surrounds the cuvette. The "copying process" is thus significantly improved not only with regard to the inclination with respect to the normals to the cuvette wall of the sample cuvette, but also with regard to the position of the overlap volume. According to the method described in the application, it is not necessary to use a cylindrical bath filled with liquid. However, this method may also be carried out using such a bath.

A further step of the method, which is schematically illustrated in FIG. 22, is carried out in such a way that the cuvette containing a slightly turbid liquid is placed in a cylindrical translucent container, and a readjustment is then performed. It is advantageous to use glass fibers together with integrated lenses as the detection optics. The lenses are generally positioned so that they focus the admitted light on the core of the glass fiber. It is advantageous to use single-mode fibers as the glass fibers. Ideally, such fibers admit only parallel light beam bundles. It is advantageous to use gradient index lenses (GRIN lenses) as the lenses. Glass fiber systems having integrated GRIN lenses in ready-made form may be used. For single-mode fibers having integrated GRIN lenses, however, the detection characteristics are divergent; that is, the beam bundle coupled in the single-mode fiber is not perfectly parallel, but instead typically has an aperture angle of 0.3°. To eliminate this shortcoming and to limit the region from which the scattered light can reach the glass fiber, the test container may be a cylindrical translucent container filled with liquid, or may be situated in a cylindrical translucent container filled with liquid. The radius of this container is at least small enough so that the divergence of the detected beam bundle is offset perpendicularly to the longitudinal axis of the cylindrical container; that is, the glass fiber admits only those portions of the light scattered from the overlap region that comprise parallel beam bundles. It is also advantageous to select the radius of the cylindrical container to be even smaller, so that the glass fiber admits light that is perpendicular to the longitudinal axis of the cylindrical container and that comprises a convergent beam bundle. Thus, the dimensions of the overlap region of the detection optics may be reduced perpendicular to the longitudinal axis of the cylinder container.

The described adjustment method may also be used for angle-dependent analyses.

The generic devices are designed in such a way that they have components on the illumination side and on the detection side. Although these are securely attached to the base plate of the device, their positioning, in particular with respect to the adjustment of their optical and physical magnitudes, is not suited for continuous operation under varying conditions. For this reason the generic devices are not usable for measurement locations which are variable, since a laborious adjustment procedure must be performed each time before the device is used for the measuring operation. To ensure a user-friendly device it is important to associate individual components with one another so that the position of the laser beams with respect to the optical plane formed by the base plate remains unchanged, thus assuring that the illuminated volume and the detected volume, and thus the incident beams and the detected scattered light, originate from the same location of the sample. It is essential that the point of intersection of the beams illuminating the sample remains constant, and that the scattered light transmitted to the detection optics at a fixed scattering angle originates from a sample volume that is always constant. The detection optics and the amplitude of the cross-correlation functions must also remain constant during the measuring operation and while the device is being used. To this end, the positioning of the detection optics and of the mirror situated upstream must remain constant. The construction of the device according to the application, by which the positioning of individual components remains constant and the detection optics are self-readjustable, allows the measurements to be reliably carried out.

To this end, a beam splitter arrangement is used to produce parallel laser beams, the beam splitter being situated in a positioning fixture so that its position with respect to the base plate does not change, that is, so that the beam guiding of the parallel beams and the position of the parallel beams with respect to the optical plane remain unchanged. In one advantageous embodiment, the invention provides that a beam splitter plate which requires no adjustment steps is placed at a fixed angle in a positioning fixture, thereby allowing the beam guiding to be fixedly positioned. In this embodiment the invention provides for a glass prism to be fixedly positioned on the base plate, the glass prism splitting the laser beam while simultaneously inclining the two emerging beams in such a way that they intersect on the central axis of the cuvette. It is particularly advantageous in the event of a maladjustment to automatically readjust the detection optics using a motor controlled by intelligent software. Alternatively, glass fiber fixtures are used which, although displaceable for the purpose of adjustment, remain fixedly positioned during continuous operation of the device.

In one advantageous embodiment of the invention, it is provided that a translucent plate having plane-parallel front and back sides acts as a beam splitter, whereby a light beam to be split into two parallel light beams strikes the front side of the plate and exits the back side of the plate as two parallel beams. To this end, the front side of the plate is fully mirror-coated in the region that lies outside the beam incidence. The back side of the plate is semi transparently mirror-coated in the region of the emergent light beam. To change the angle of incidence of the light beam, and thus to change the distance between the emerging light beams, the plate is tiltable about a tilting axis. The tilting axis lies in the plane of extension of the plate, parallel to the plane-parallel lateral faces of the plate, and intersects the point of incidence of the incident light beam. Using only a single plate, it is thus possible to carry out measurements using parallel beams having a variable distance from one another merely by changing the position of the angle of inclination of the plate in the positioning fixture, or by using positioning fixtures having different angles of inclination.

It is particularly advantageous to provide the front side of the plate with antireflective coating in the region of the incident light beam. Loss of intensity in this region is thus avoided. The same applies for the antireflectively coated region on the back side.

In this embodiment, an overlap region is present in which, as viewed perpendicular to the plate, the fully mirror-coated region on the front side overlaps with the semi transparently mirror-coated region on the back side.

The beam splitting is carried out according to the invention as follows:

The incident light beam strikes the front side of the plate, passes through the plate, and is partially reflected and partially transmitted upon striking the semi transparently mirror-coated region on the back side of the plate. The transmitted beam undergoes only a spatial displacement with respect to the incident light beam, and the two beams have the same direction. The beam reflected at the semi transparently mirror-coated region strikes the fully mirror-coated region on the front side, whereupon it is re-reflected and then exits, parallel to the incident light beam and the emergent light beam, in the antireflectively coated region on the back side of the plate.

It is additionally provided that the overlap region is designed so that the semi transparently mirror-coated region on the back side proceeds from a line corresponding to the dividing line between the fully mirror-coated region and the region of the incident beam, or, respectively, the antireflectively coated region on the front side, and extends in the direction of the fully mirror-coated region on the front side and meets a line parallel to the dividing line whose distance from the dividing line depends on the thickness of the plate, the angle of incidence of the beam, and the refractive index of the plate material. The plate is tiltable about the tilting axis in order to change the angle of incidence of the beam, and at the same time is displaceable along the tilting axis. Thus, for a wide range of values for the angle of incidence of the beam, the transmitted beam at the back side of the plate always strikes the semi transparently mirror-coated region and exits the plate, and the light beam reflected from the semi transparently mirror-coated region on the back side and from the fully mirror-coated region on the front side always strikes the antireflectively coated region and exits the plate. This allows the distance between the parallel beams which are produced to be continuously adjusted over a wide range of values. This is dependent on the plate thickness, the refractive index of the plate material, and the tilting angle of the plate or the angle of incidence of the light.

In one advantageous embodiment of the invention, the beam splitter plate is securely mounted in a fixture which is placed in the portable device. This fixture is advantageously mounted in a position which with respect to the optical plane has an angle of inclination less than 45°. In this arrangement, the beam reflected at the glass/air transition at the front side is diverted in a direction perpendicular to the optical plane, thus allowing the reflected light to be easily detected.

In the embodiment, the invention provides that no overlap region is present, that is, that the semi transparently mirror-coated region on the back side corresponds to the region of the beam incidence (the antireflectively coated region) on the front side, and the fully mirror-coated region on the front side corresponds to the antireflectively coated region on the back side. In this embodiment, the plate is tiltable about the tilting axis in order to change the angle of incidence of the beam, and is displaceable perpendicular to the direction of the incident beam, in the plane perpendicular to the tilting axis, in such a way that the point of incidence of the light beam and the tilting axis corresponding to the change in the angle of incidence of the beam may be separated at a distance from one another. It is also provided that the plate is tiltable in order to change the angle of incidence of the beam, and is displaceable in a direction perpendicular to the tilting axis and to the direction of the incident beam. This tilting and corresponding displacement of the plate allows the distance between the emerging parallel beams to be adjusted over a wide range, from very small to very large distances.

If the plate is situated in a fixture that allows the plate position to be continuously changed, the distance from the beams may be continuously changed.

For the production of two parallel beams, it is essential that the overlap region, viewed perpendicular to the plate, is at least as wide as the distance between the point of emergence of the transmitted beam and the point of incidence of the incident beam, but smaller than the distance between the latter-referenced point and the point of emergence of the beam which is transmitted and which is reflected in the semi transparently mirror-coated region on the front side and in the fully mirror-coated region on the back side. As a result of the embodiment according to Claims 31, 32, and 33 it is possible to achieve a maximum tilting angle, and the emerging beams always strike the semi transparently mirror-coated region or the antireflectively coated region on the back side. The described design is essential in order to design this region with a given plate thickness and the specified plate material, that is, the specified refractive index, to be as large as possible.

It is advantageous for the translucent plate to be designed as a glass plate.

The antireflectively coated, semi transparently mirror-coated, and fully mirror-coated regions are prepared by coating the plate with aluminum or silver, or with a dielectric coating.

The device according to the invention is described in more detail with reference to the drawings and examples.

FIG. 6 shows a section through the beam splitter plate, with the beam path sketched in;

FIG. 8 shows a schematic illustration of the plate movement for various tilting angles;

Figure 16:
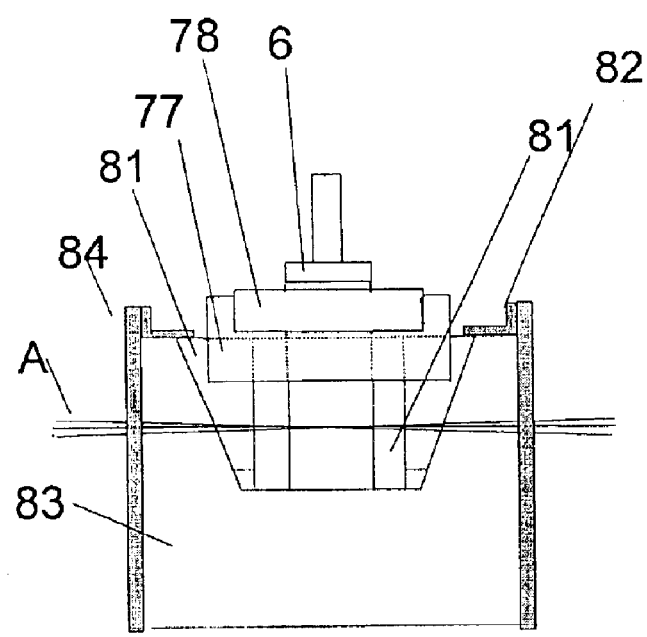
FIGS. 16 and 19 show a side view of various cuvette fixtures.
Figure 17:
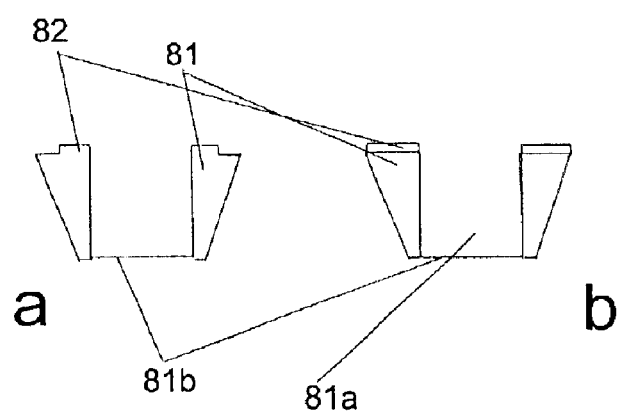
Figure 18:
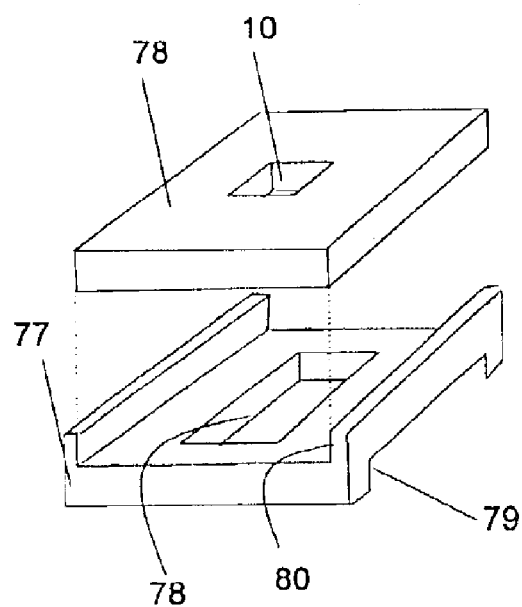
Figure 19:
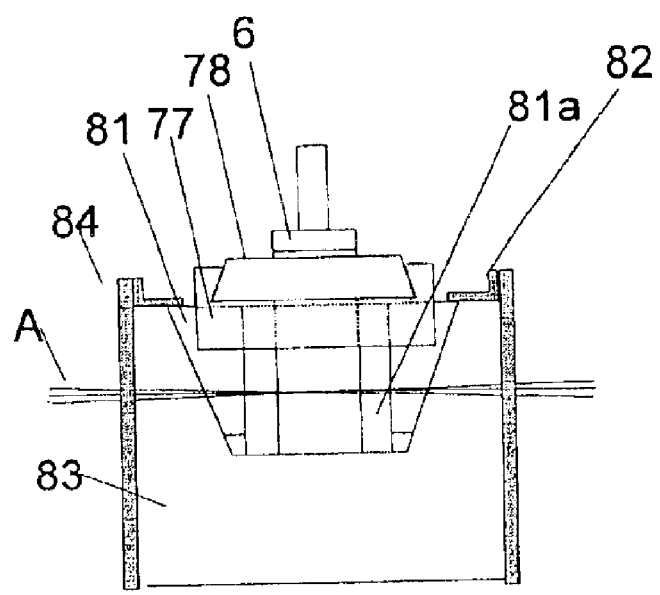
Figure 20:
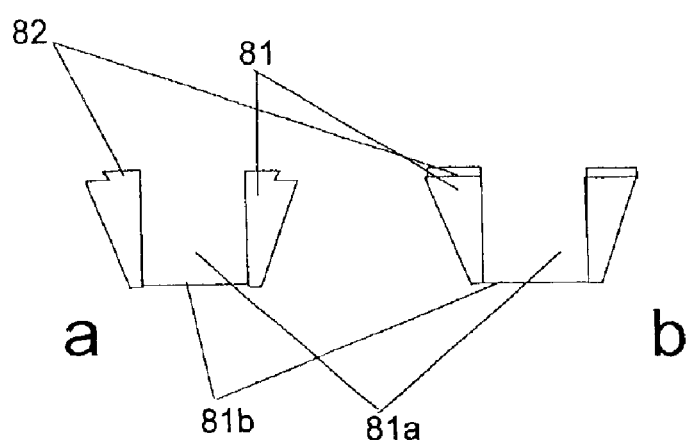
Figure 21:
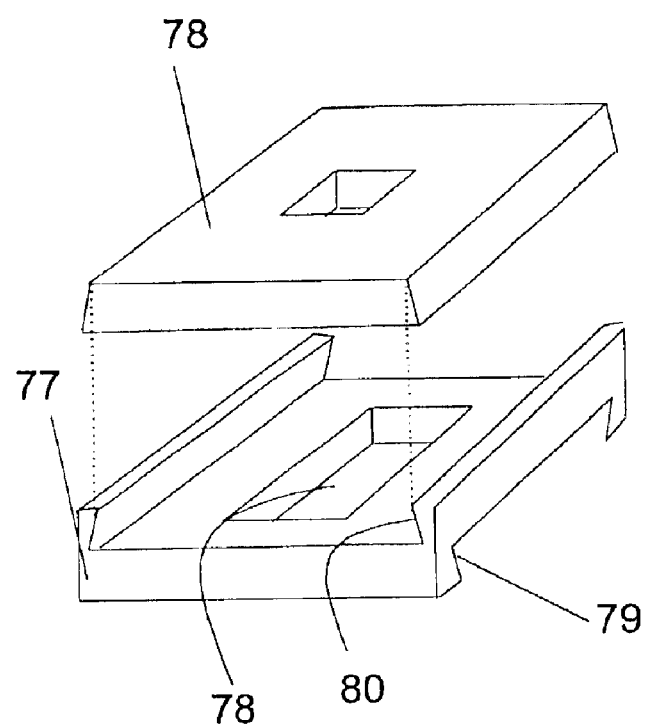
Figure 22:
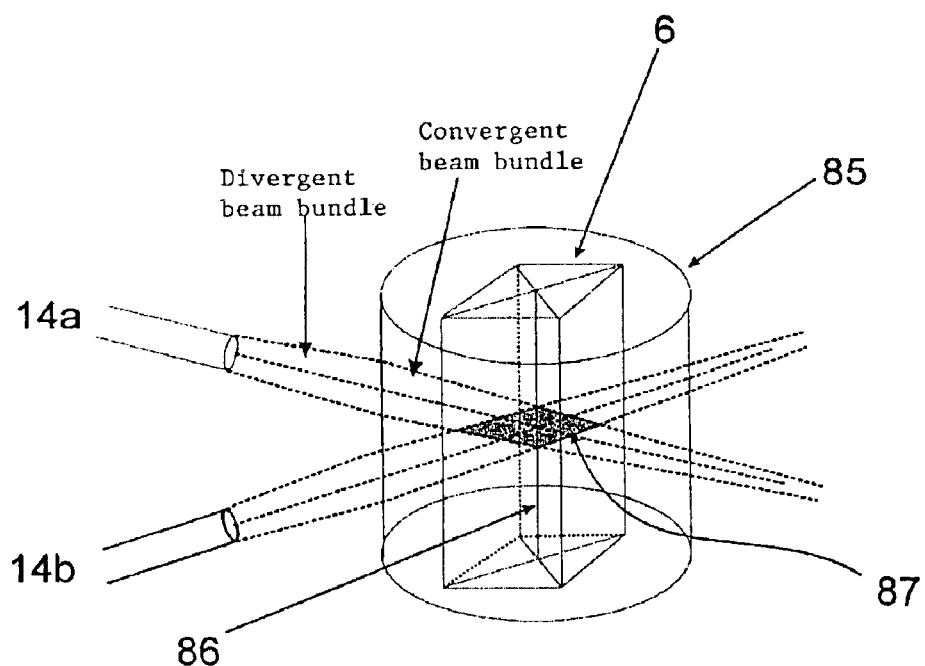
Figure 23:
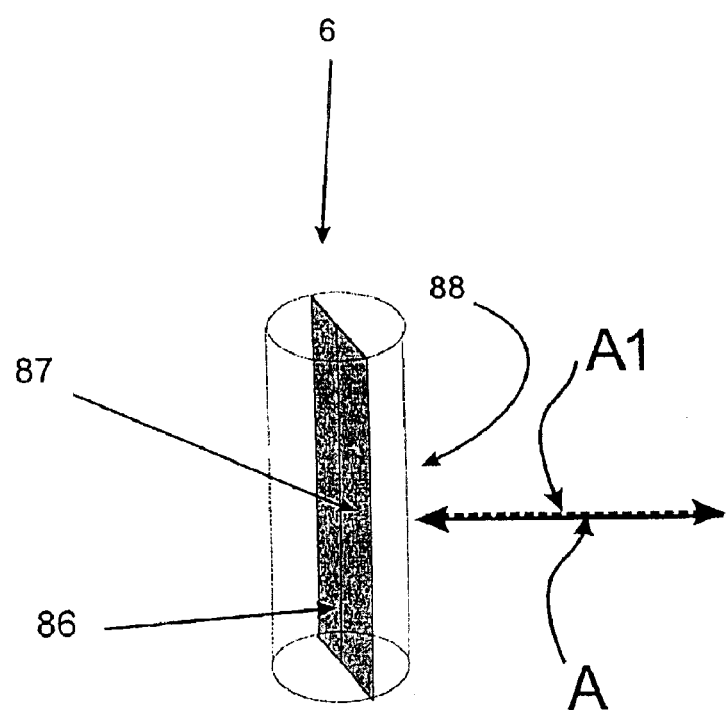
Figure 24:
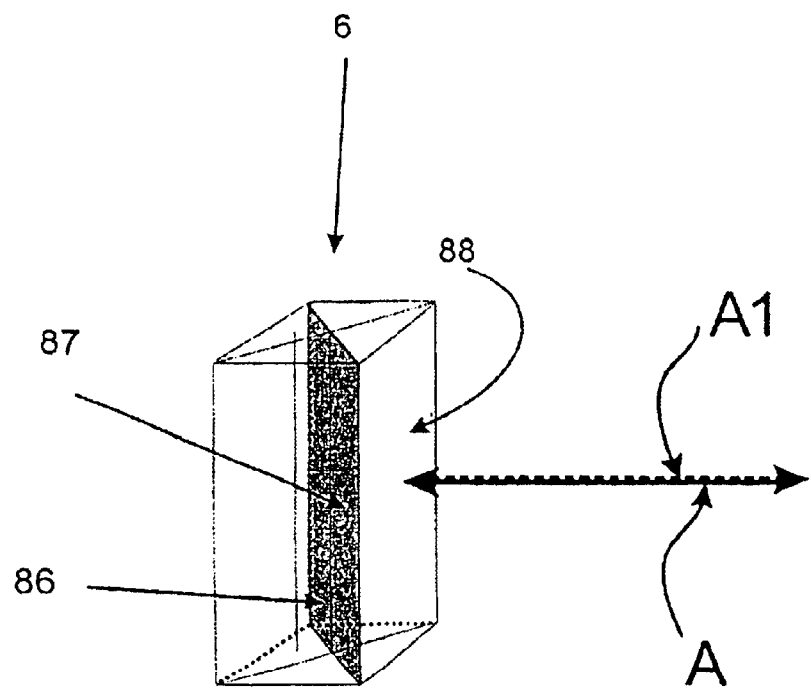

FIGS. 17, 18, 20, and 21 show various embodiments of the x-y displacement position elements of the cuvette fixture from FIG. 16;

FIG. 22 shows a schematic illustration of the beam path during adjustment, using a cylindrical bath container;

FIG. 23 shows a schematic illustration of the beam path, using a cylindrical cuvette; and FIG. 24 shows a schematic illustration of the beam path, using a rectangular cuvette.

Figure 1:
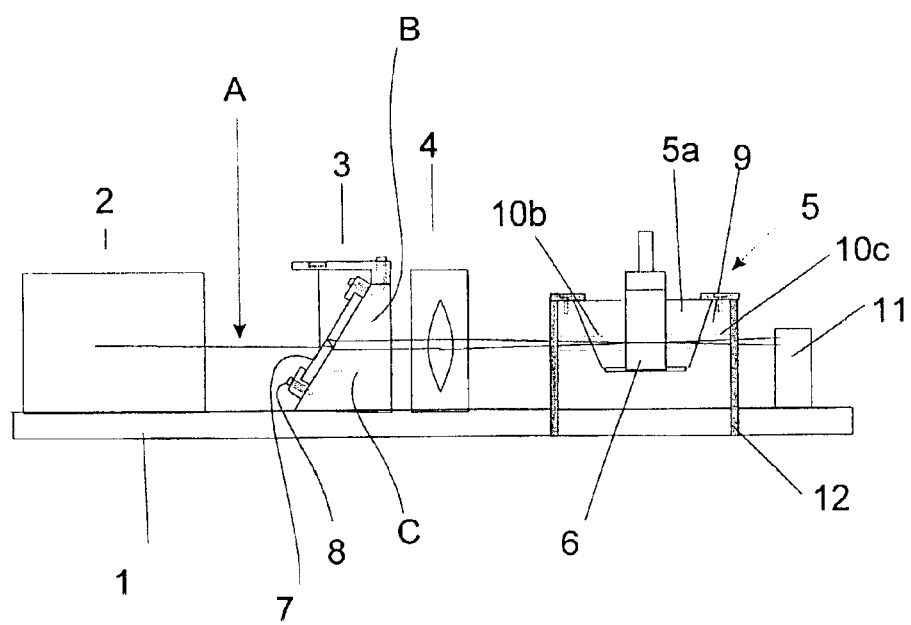
FIG. 1 shows a schematic illustration of the side view of the device.
Figure 2:
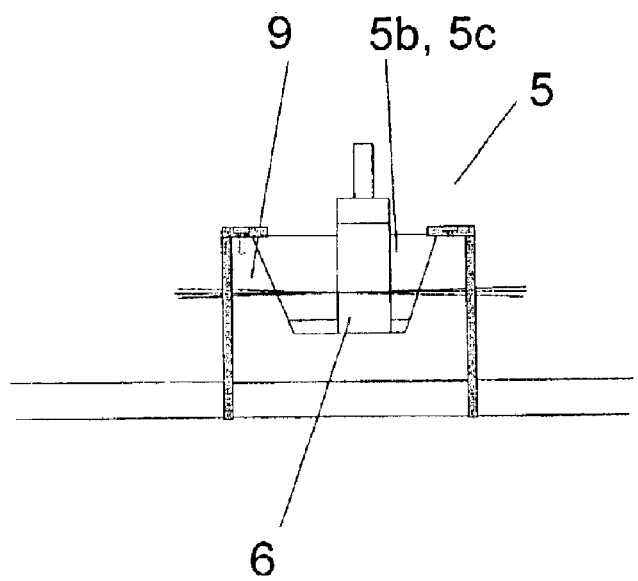
FIG. 2 shows a front view of the cuvette fixture, with different arrangements of the intersection regions of the laser beams.

FIG. 1 shows a schematic illustration of the device according to the invention in a side view. The device has a base plate 1, a laser 2, a beam splitter 3, a lens 4, and a fixture 5 for a cuvette 6. Laser beam A may be aligned parallel to base plate 1 and perpendicular to the walls of cuvette 6, using appropriate tilting devices or fixtures which are known for such purposes. The laser beam strikes a beam splitter 3 in the form of a glass plate 7 which splits laser beam A by means of a suitable coating into two parallel laser beams B, C of practically equal intensity, laser beams B, C being displaced with respect to incident laser beam A but having the same direction as the incident laser beam. Glass plate 7 is situated in a positioning fixture 8 by means of which glass plate 7 is stably mounted to protect against shocks, at an angle inclined with respect to the base plate which is specified for the analyses. Both laser beams B, C are focused using a lens 4 so that the two laser beams overlap inside cuvette 6. Cuvette fixture 5 comprises a fixture 5a, 5b, 5c, conforming to the shape of the cuvette, which is situated in an additional fixture 9. In one advantageous embodiment of the invention, the external dimensions of fixtures 5a, 5b, 5c run conically, conforming to the internal dimensions of fixture 9, thereby ensuring a central positioning of fixtures 5a, 5b, 5c. In addition, in one advantageous embodiment of the invention fixtures 5a, 5b, 5c are provided in such a way that the overlap region of both laser beams B, C is situated in the center of cuvette fixture 5a, in a corner of cuvette fixture 5b, and at a small distance from a cuvette wall fixture 5c. It is advantageous for the adjustment if the point of intersection of the laser beams lies on the central axis of the cuvette, since in this way the point of intersection can be localized most easily. In analyses using turbid liquids, the point of intersection may also be a corner of the cuvette or at a small distance from the cuvette wall. Cuvette fixture 5 has boreholes. Borehole 10a is provided in such a way that both of the incident laser beams are able to illuminate cuvette 6. By means of another borehole 10c the transmitted laser beams meet at location 11 on a beam stopper or a laser intensity measuring device.

Figure 3:
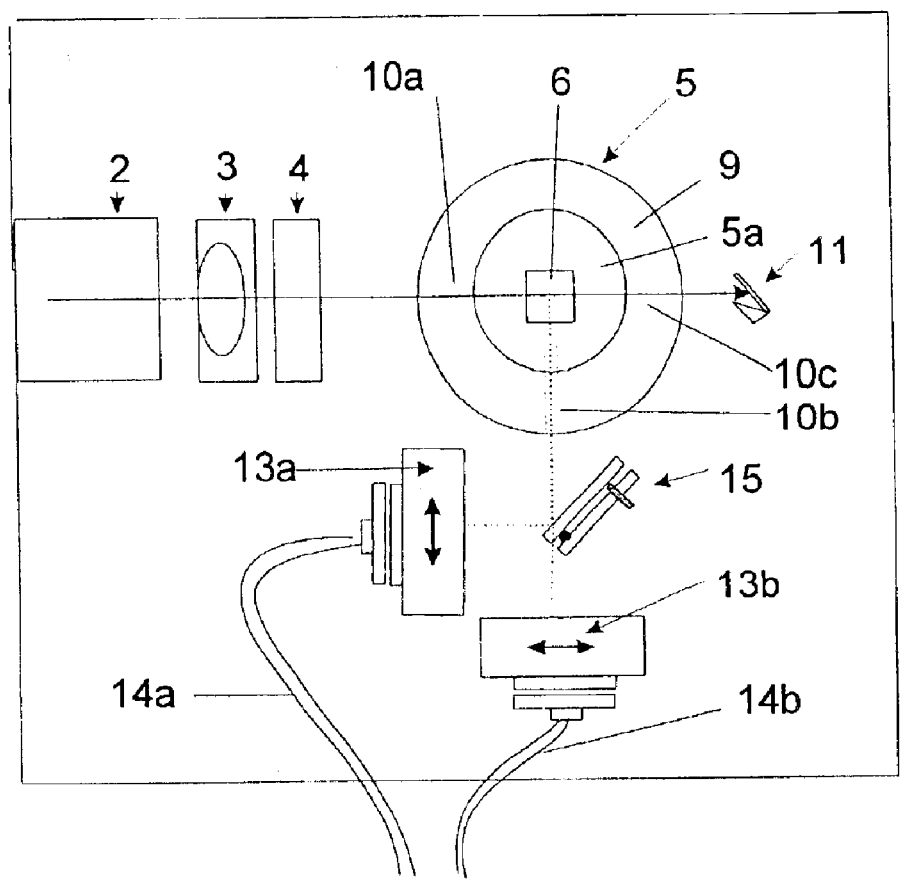
FIG. 3 shows a top view of the device.
Figure 4:
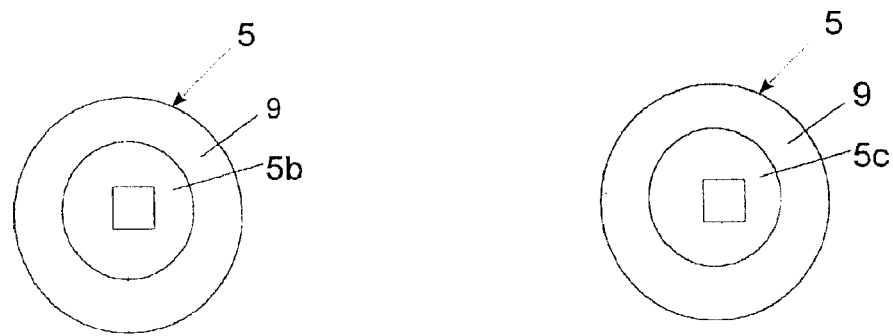
FIG. 4 shows a top view of the cuvette, with different arrangements of the intersection regions of the laser beams.

As shown in FIG. 3, borehole 10b allows the scattered light to exit fixture 5 in a direction that is perpendicular to incident laser beam A. The plane defined by the direction of the incident laser beam and the direction perpendicular thereto in which the scattered light exits cuvette fixture 5 is the "optical plane." Fixtures 5a, 5b, 5c are provided in such a way that the longitudinal edges of cuvette 6 are perpendicular to the optical plane. A portion of the scattered light strikes mirror 15, which diverts the scattered light to glass fiber fixture 13a so that the intensity of the scattered light can be collected by glass fiber 14a. Mirror 15 is situated in a tilting fixture by which the mirror can be tilted about two tilting axes. One of the tilting axes allows tilting about an axis which is perpendicular to the optical plane. The other tilting axis is parallel to the optical plane and to the plane of extension of the mirror. Both axes pass through a common point located directly behind the mirror. Another portion of the scattered light exiting borehole 10b strikes a glass fiber fixture 13b in such a way that the intensity of the scattered light can be admitted by a glass fiber 14b. Glass fiber fixtures 13a, 13b and mirror 15 are adjusted so that only that portion of the scattered light having a geometry congruent with that of the incident laser beams can be admitted by glass fibers 14a, 14b. That is, among other factors, the tilting angle of glass fibers 14a, 14b with respect to the optical plane is congruent with the tilting angle under which both incident laser beams B, C are tilted with respect to the optical plane by the focusing effect of lens 4. In one advantageous embodiment of the invention, fixtures 9, 5a, 5b, 5c are temperature-controllable and are surrounded by an insulating layer 12.

Figure 5:
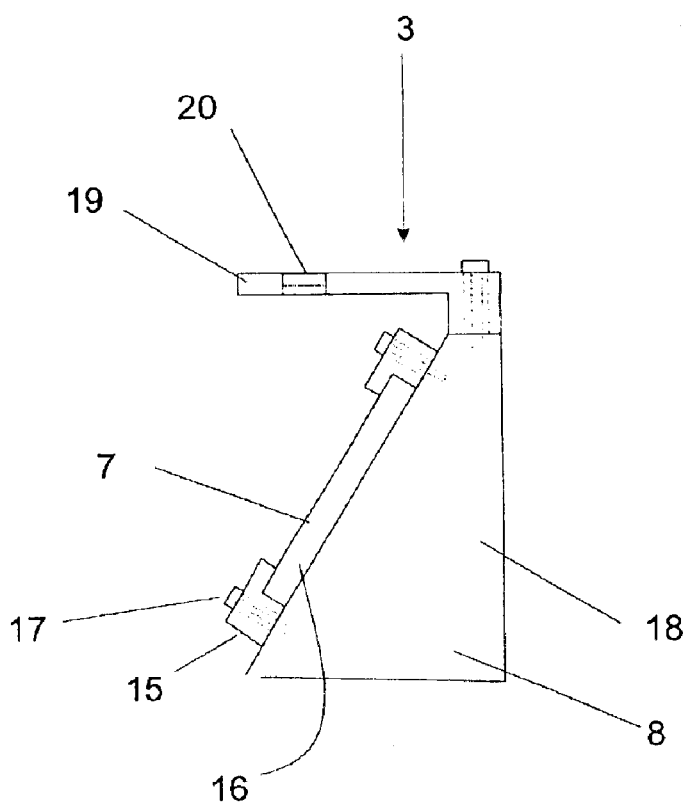
FIG. 5 shows a side view of the positioning fixture for the beam splitter.

FIG. 5 shows beam splitter fixture 8 in the side view. Glass plate 7 is situated in an annular socket 15 which is mounted on inclined plane 16 of positioning fixture 8 by a fastening screw 17 in such a way that glass plate 7 is pressed against inclined plane 16. Positioning fixture 8 has a borehole 18 through which parallel laser beams B, C exiting glass plate 7 are admitted. One advantageous embodiment of beam splitter fixture 8 has a fixture 19 positioned on the upper end in which a laser power measuring device 20, for example a diode, is mounted.

Figure 6:
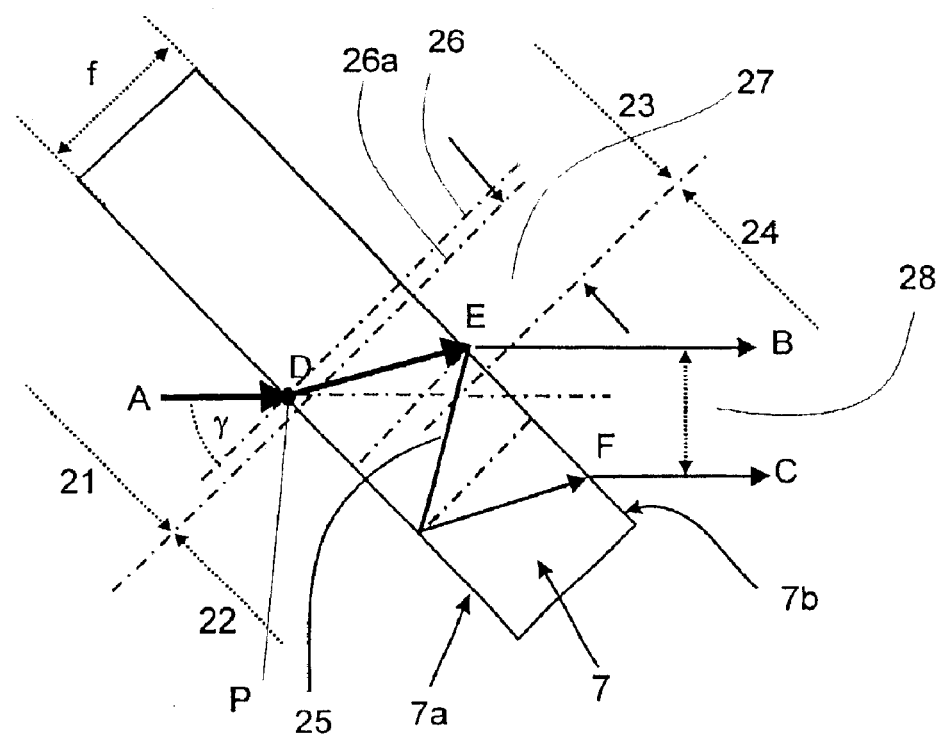

Beam splitter plate 7 illustrated in FIG. 6 has a plane-parallel front and back side 7a, 7b on which suitable coatings are applied. Front side 7a of plate 7 is antireflectively coated in region 21 of incident light beam A by application of a suitable coating, and in the remaining region, that is, in region 22 (outside incident light beam A), is fully mirror-coated using a suitable coating. Back side 7b of plate 7 is semi transparently mirror-coated in one region 23 and in another region 24 is antireflectively coated. Plate 7 has a thickness f. Incident light beam A enters at point D and is partially reflected and partially transmitted at point E by semi transparently mirror-coated region 23 on back side 7b of plate 7. Transmitted beam B is only spatially displaced with respect to incident light beam A, and the direction of transmitted beam B is the same as that of incident light beam A. Beam 25 which is reflected from semi transparently mirror-coated region 23 on back side 7b is re-reflected by fully mirror-coated surface 22 on front side 7a of plate 7, and exits plate 7 at point F (beam C) parallel to beams A, B.

Plate 7 can be tilted about tilting axis P. Tilting axis P lies in the plane of extension of plate 7 and runs parallel to its lateral surface, that is, parallel to front side 7a and back side 7b and perpendicular to the plane of the incident beam, through point of incidence D of light beam A. Angle of incidence γ of light beam A at point D is the angle between incident light beam A and normal 26 to lateral surfaces 7a, 7b. This angle γ is at the same time the tilting angle of plate 7. Plate 7 illustrated in FIG. 6 also has an overlap region 27. Overlap region 27 is the region in which, viewing plate 7 perpendicularly, fully mirror-coated region 22 on front side 7a and partially mirror-coated region 23 on back side 7b overlap one another. Dividing line 26a separates regions 21 and 22. By tilting plate 7 and thereby changing angle γ, distance 28 between the two parallel light beams B, C exiting plate 7 is changed over a specific range of values and, for example, adjusted as required. Continuous tilting of plate 7 and, thus, continuous changing of angle γ also causes distance 28 between beams B and C to continuously change. This change in beam distance 28 is determined by the value of angle γ and the geometric relationships between the position of tilting axis P or normal to plate 26 which passes through point of incidence D of light beam A, and points of emergence E and F of parallel beams B, C. To produce two parallel beams, overlap region 27 must be at least as wide as the distance between tilting axis P or normal 26 to the plate and point of emergence E of transmitted beam B, but smaller than the distance between tilting axis P and point of emergence F of second parallel beam C.

Figure 7:
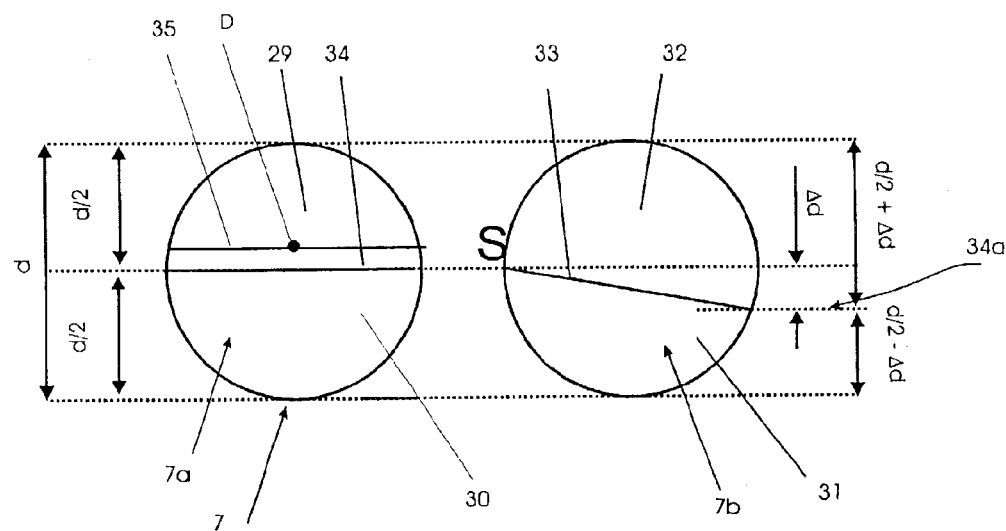
FIG. 7 shows an illustration of a coating arrangement for a circular plate.
Figure 6:
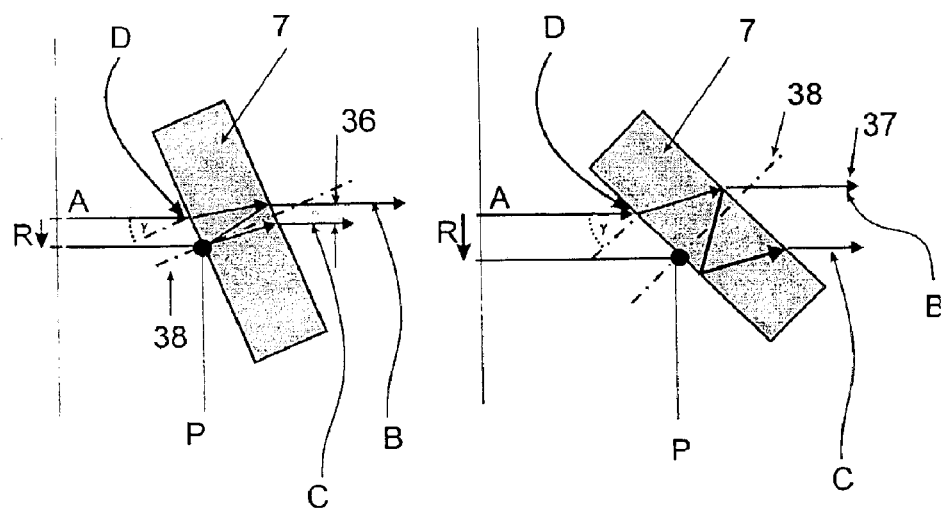

FIG. 7 illustrates an embodiment of translucent plate 7 which allows plate 7 to be used for the largest possible number of angles γ over a very wide range of values. To this end, an antireflectively coated region 29 and a fully mirror-coated region 30 are respectively provided on each half of front side 7a of plane-parallel plate 7. An antireflectively coated region 31 and a semi transparently mirror-coated region 32 are situated on back side 7b. As illustrated in FIG. 7, boundary line 33 runs between these two regions 31, 32 on back side 7b of plate 7 in such a way that said boundary line has on the one end a point of intersection S with a line which corresponds to dividing line 34 on back side 7b of plate 7 between the two regions 30, 29. The other end of boundary line 33 has a point of intersection with a line 34a running at a distance Δd parallel to dividing line 34. Distance Δd is dependent on thickness f of the plate, maximum tilting angle γ, and the refractive index of the plate material, as follows:

$$\Delta d = d \tan(\arcsin(\sin \gamma_{max}/n))$$

On the back side 7b, the antireflectively coated region 31 proportionately spans the smaller region. Viewing plate 7 perpendicularly, the semi transparently mirror-coated region 32 on the back side 7b is situated in the same circular segment as the antireflectively coated region 29 on the front side 7a, and the antireflectively coated region 31 on the back side 32 [sic] is situated in the same circular segment as the fully mirror-coated region 30 on the front side 7a. Plate 7 having such a design is mounted so that it is displaceable along the tilting axis 35 running through the point of incidence D of the light beam, and as a result of the combined displacement and tilting movements the distance between the exiting parallel beams is continuously adjustable over a wide range. Distance a between the exiting beams is determined as follows:

$$a = 2f \cos \gamma \tan(\arcsin(\sin \gamma_{max}/n))^{0001}$$

[0001] Translator's note: Subscript "max" was apparently omitted after "γ" (see previous similar formula).

FIG. 8 shows an embodiment of plate 7 in which both regions on the front side and both regions on the back side correspond to one another, so that there is no overlap region. As shown in FIG. 8, in order to achieve a large range in the change of distance 36, 37 between exiting beams, plate 7 is displaced in a direction R, perpendicular to the direction of incident beam A, in such a way that point of incidence D of incident light beam A and tilting axis P corresponding to the change in angle of incidence γ of the beam are separated by a distance, so that transmitted beam B always strikes the semi transparently mirror-coated region on the back side and the other parallel beam C strikes the antireflectively coated region on the back side.

There are two embodiments of the glass fiber fixtures on the detection side: in one embodiment glass fiber fixtures 13a, 13b are used which allow an extremely stable manual positioning of the glass fiber optic in the smallest space, all necessary degrees of freedom being available. This embodiment is costly. The second embodiment is used for adjusting glass fiber fixtures 13a, 13b and components of mirror 15 for fine self-adjusting.

Figure 9:
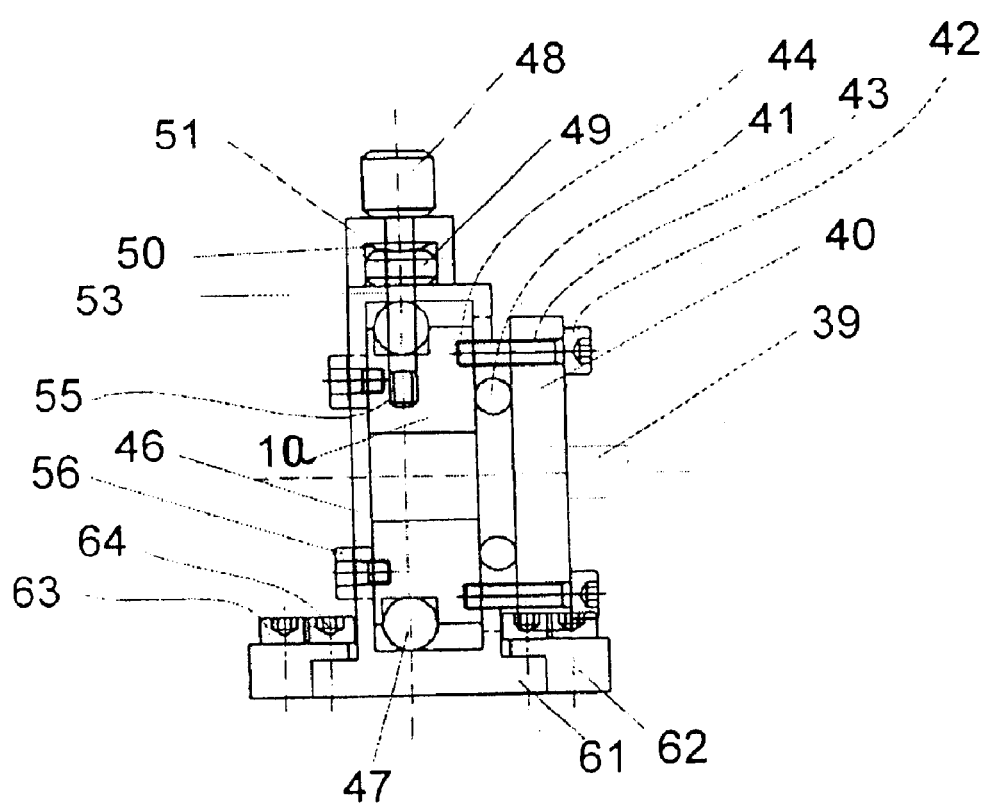
FIG. 9 shows a side view of the glass fiber fixture.
Figure 10:
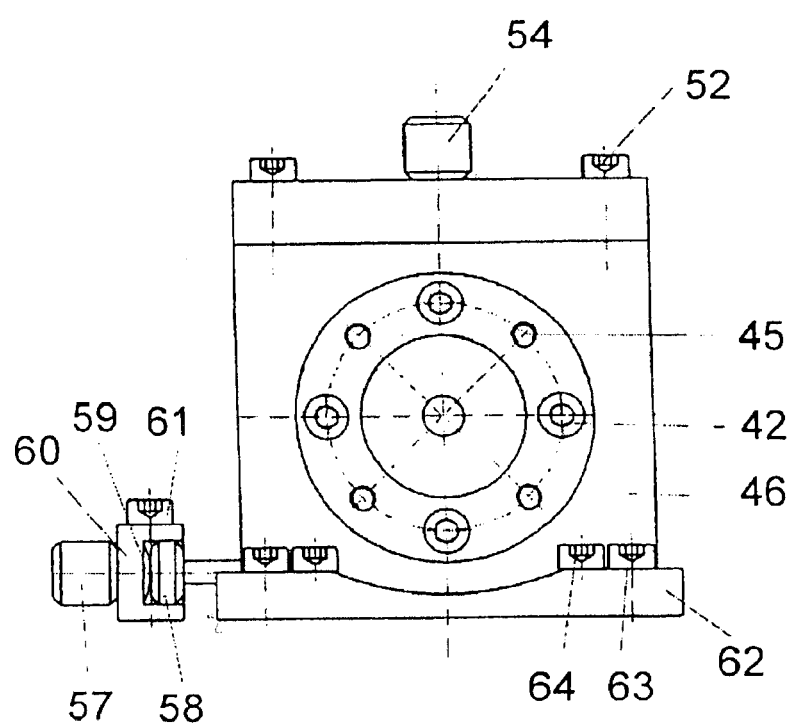
FIG. 10 shows a front view of the glass fiber fixture from FIG. 9.

FIGS. 9 and 10 show the construction of glass fiber fixtures 13a, 13b for the first embodiment. The glass fibers are mounted using a suitable bushing 39. Bushing 39 is situated on a plate 40 which is tiltable with respect to base plate 1a. The tilting is made possible by the fact that a ring 41 made of a rubber-like material is positioned between plate 40 and base plate 1a, and plate 40 may be pressed against base plate 1a by screws 42. For this purpose boreholes 43 are provided in plate 40 through which screws 42 are passed, and threads 44 are provided on base plate 1 to tighten screws 42. To increase stability after the adjustment is made, plate 40 is fixed by a lock nut against base plate 1a by fastening screws 45. Base plate 1a is situated in an additional fixture 31. Base plate 1a is displaceable via a system comprising an adjustment screw 48, a locking ring 49, a disk spring 50, and a screw receptacle 51 which is provided on fixture 46 by screws 52. The direction of displacement runs perpendicular to the plane of extension of base plate 1a and perpendicular to the optical plane. Boreholes 53 are provided in fixture 46 through which screws 54 are introduced, and base plate 1a is provided with a thread 55 which enables the screws to be tightened. Base plate 1a may be screwed down on fixture 46 using fastening screws 56. Fixture 46 along with base plate 1a and plate 40 is also displaceable in a direction running parallel to the optical plane and to the plane of extension of base plate 1a. To this end, on fixture 46 there is situated an additional system comprising an adjustment screw 57, a locking ring 58, a disk spring 59, and a screw receptacle 60 which is provided by screws 61 on base plate 1 of the device. In addition, a tab 61 which can be pushed into a guide 62 is situated on fixture 46. Guide 62 is fastened by screws 63 to base plate 1. Tabs 60 [sic] may be affixed to base plate 1 using fastening screws 64 after the adjustment is completed.

For the self-adjusting system, motorized drives and piezoelectric elements are used for the displacement of base plate 1a. To this end, known minipositioning units are used which are mounted so that base plate 1a may be displaced in a direction that is perpendicular to the optical plane, and may be displaced in another direction running parallel to the optical plane and to the plane of extension of base plate 1a. Motorized drives and piezoelectric elements are likewise used for the tilting of mirror 15. Using intelligent software control, the optical components are adjusted in an iterative process in such a way that a maximum signal amplitude is achieved. In addition, the software control ensures increased long-term stability of the optimized adjustment.

Figure 11:
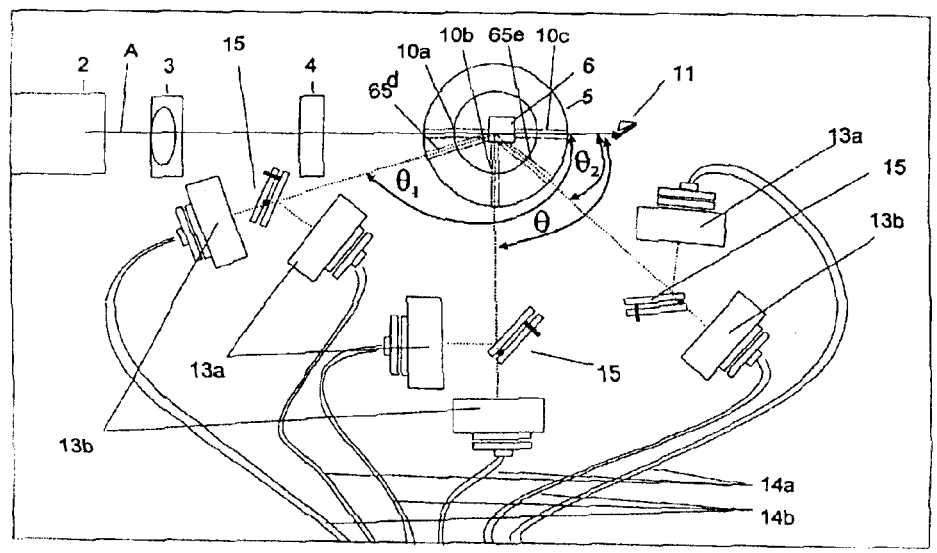
FIG. 11 shows an illustration of the illumination side and the detection side for detecting different fixed scattering angles.

FIG. 11 shows a further advantageous embodiment of the device illustrated in FIG. 3. An additional borehole 65d is provided through which the scattered light exits at an angle $\theta_1$ which is greater than 90°, and the scattered light exits borehole 65e at an angle $\theta_2$ which is less than 90°. As a result of the possibility of examining the characteristic of the scattered light at $\theta=90°$ in addition to the backward direction $\theta_1$ and the forward direction $\theta_2$, more information is obtained on the sample to be examined. For each of these angles $\theta=90°$, $\theta_2$, $\theta_1$, a system is present comprising mirror 15, glass fiber fixtures 13a, 13b, and glass fibers 14a, 14b. A portion of the scattered light strikes mirrors 15, which divert the scattered light to glass fiber fixtures 13a in such a way that the intensity of the scattered light can be collected by glass fibers 14a. The position of elements 15, 13a, and 13b with respect to one another may be variable, and may be achieved with a view to economizing the distribution of space. Mirrors 15 are situated in tilting fixtures which enable each of mirrors 15 to be tilted about two tilting axes. One of the tilting axes allows tilting about an axis that is perpendicular to the optical plane. The other tilting axis is parallel to the optical plane and to the plane of extension of the mirror. Both axes run through a common point located directly behind the mirror. Glass fiber fixtures 13a, 13b are adjusted in such a way that only that portion of the scattered light having a geometry congruent with that of the incident laser beams can be admitted by the glass fibers. That is, the tilting angle of glass fibers 13a, 13b with respect to the optical plane is congruent with the tilting angle at which the two incident laser beams are tilted with respect to the optical plane by the focusing effect of lens 4.

Figure 12:
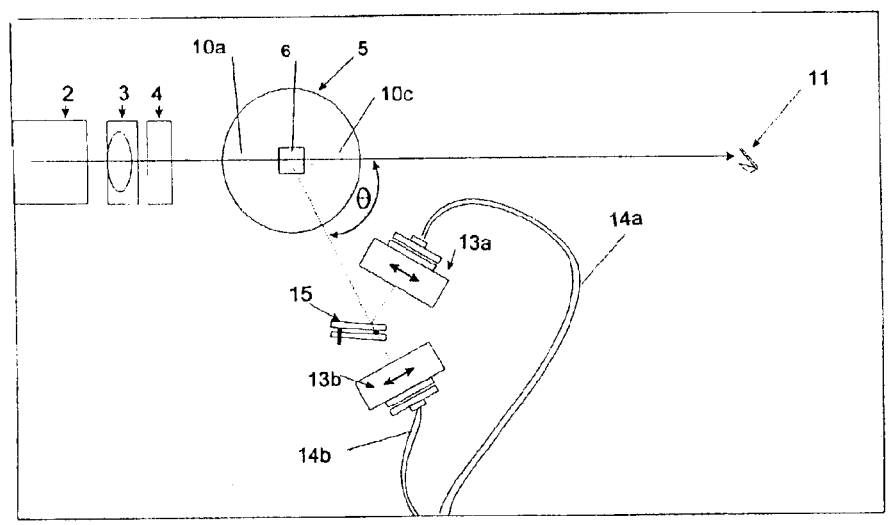
FIG. 12 shows a top view of a further embodiment of the arrangement for variable adjustment of the scattering angle.

FIGS. 12 (top view) and 13 (side view) show a further advantageous embodiment of the invention for variable scattering angle $\theta$. In this case additional components are required which generally elevate the scattering planes. Thus, the components comprising laser 2, beam splitter 3, and lens 4 are lifted to the proper height by means of suitable substructures 66. A system comprising mirror 15 and glass fiber fixtures 13a, 13b is situated on a plate 67 connected to a rotating device 68. In this manner the components comprising mirror 15 and glass fiber fixtures 13a, 13b may be rotated about the common centerpoint of fixture 69 and of rotating device 68. Fixture 69 preferably includes a cylindrical glass container 70 in the center of which sample cuvette 6 is placed. Fixture 69 has a slot 71 at a suitable height so that the scattered light can reach the glass fibers. In an advantageous embodiment of the invention the fixture is situated on a platform 72 designed so that fixture 69 may be placed and titled in such a way that the longitudinal axis of glass cuvette 70 is perpendicular to the optical plane, and the centerpoint of the cuvette is congruent with the point of rotation of rotating device 68. In addition, it is advantageous if platform 72 and rotating device 68 are positioned on an additional plate 73 which may be displaced in such a way that the centerpoint of cylindrical glass container 70 as well as the centerpoint of rotating device 68 are stuck by the incident laser beams.

Figure 13:
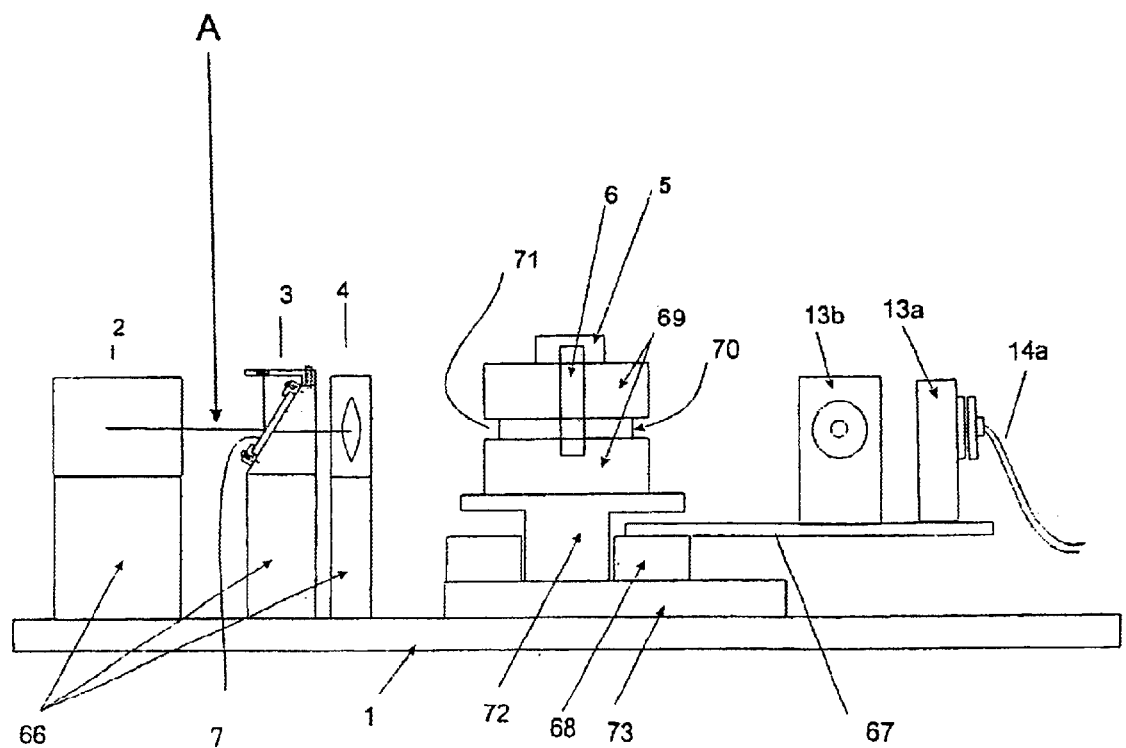
FIG. 13 shows a side view of the embodiment from FIG. 12.

For the arrangements described in FIGS. 12 and 13, the use of stable glass fiber fixtures 13a, 13b, and a stable device 3 for the beam splitting of laser beam A into two parallel laser beams B, C, in addition to the use of mirror 15 as an adjusting and separating component with a stable tilting fixture, are particularly advantageous, since shocks can occur from operation of the rotating device which could severely impair the adjustment. In the same way, in another embodiment of the invention it is particularly advantageous to equip this arrangement with motorized, controllable components for tilting of mirror 15 and for glass fiber fixtures 14a, 14b and base plate 1a, and to ensure a self-adjusting device using intelligent software.

Figure 14:
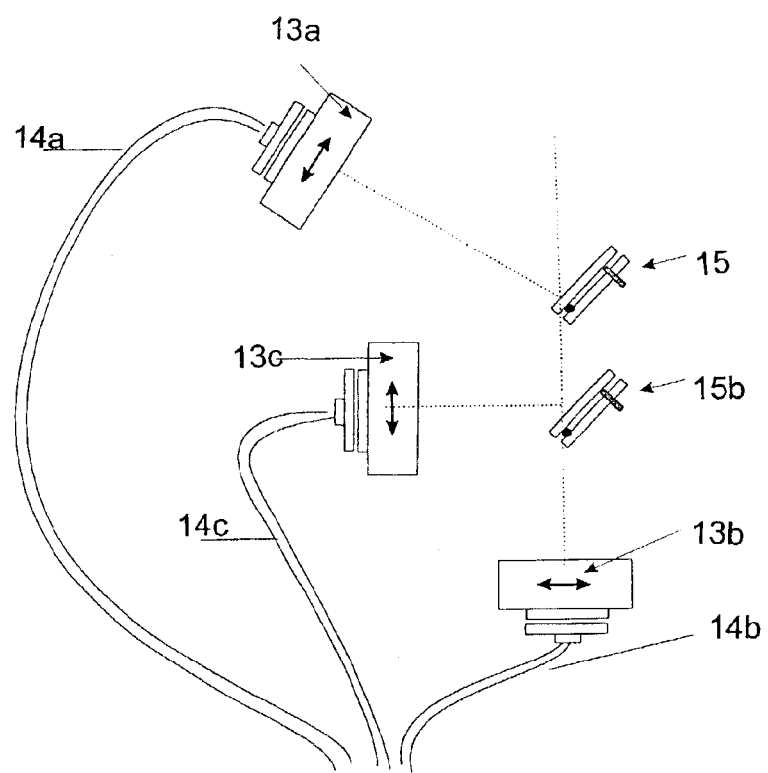
FIG. 14 shows a schematic illustration of the detection optics, with two mirrors and three glass fiber fixtures.

FIG. 14 shows a further advantageous embodiment of the invention for the arrangement of components on the detection side. By the use of the mirror as an adjusting aid and the separation of scattering planes, the components comprising glass fiber fixture 13a and glass fiber 14a may be arranged in any desired position with respect to glass fiber fixture 13b. In this manner, an additional system comprising mirror 15b, glass fiber fixture 13c, and glass fiber 14c may be readily mounted, thus providing an additional scattering plane at the same scattering angle $\theta$.

Figure 15:
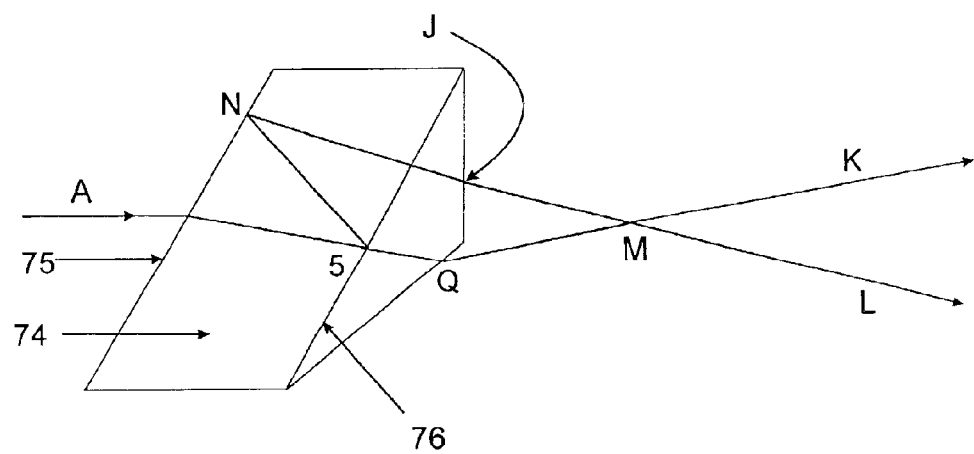
FIG. 15 shows a schematic illustration of a glass prism beam splitter, showing the beam path.

FIG. 15 illustrates a glass prism 74, with laser beam A being split into two laser beams K and L in such a way that the two laser beams overlap at a point M situated inside the illuminated sample volume. Laser beam A strikes inclined, antireflectively coated surface 75 of glass prism 74. Beam A strikes a semi transparently mirror-coated surface 76 at S.

A portion of the beam is admitted, and exits glass prism 74 at Q. The surface of the glass prism at location Q is inclined in such a way that exiting beam K passes through point M. The other portion of incident laser beam A is reflected on semi transparently mirror-coated surface 76, strikes point N on a fully mirror-coated surface, and is fully reflected there and exits glass prism 74 at J. The surface of the glass prism containing point J is inclined so that exiting beam L likewise passes through point M.

FIGS. 16 through 21 illustrate a cuvette fixture according to the invention which allows the cuvette to be displaced in the horizontal plane in the x-y direction. Cuvette 6 is situated in an x-y displacement device comprising a first, lower displacement device 77 and a second, upper displacement device 78. Upper displacement device 78 has an opening in the center so that cuvette 6 can be inserted from above in the most precise manner possible, without play. Lower displacement device 77 has an opening 78 [and] two tracks 79 and 80: lower track 79, and upper track 80 situated perpendicular thereto. Upper, first displacement device 78 is placed in upper track 80 and may be displaced in one direction. Lower displacement device 77 may be set on top of lower track 79 on a fixture 81. Fixture 81, in turn, has on its upper side an opposing track 82 which fits track 79. FIG. 17b shows the fixture from FIG. 16 in a side view. FIG. 17a shows fixture 81, likewise in a side view, but rotated by 90°. Fixture 81 has an opening 81a in which, in one advantageous embodiment of the invention, a cylindrical translucent container 81b filled with liquid is situated. In addition, fixture 81 may be pressed into overall fixture 83 using a fastening device 82.

The inner shape of the overall fixture is conical, to match the outer shape of fixture 84. In one advantageous embodiment of the invention, overall fixture 83 is situated inside an insulating layer 84.

In one advantageous embodiment of the invention, tracks 80 and/or 79 and/or opposing track 82 are designed as dovetail guides (FIGS. 19 through 21) or as a prismatic guide.

FIG. 22 schematically illustrates the beam path in the arrangement of cuvette 6 in a cylindrical bath container 85.

FIGS. 23 and 24 illustrate the alignment of a laser beam A perpendicular to the cuvette wall, as described in procedural step one. Laser beam A is reflected on the cuvette wall, which is either internally or externally mirror-coated with a black liquid. This reflected beam A1 returns in incident beam A. A mirror surface 87 placed into cuvette 6 in step three of the procedure passes through central axis 86 of cuvette 6.

What is claimed is:

1. Method of suppressing multiple scattering during examinations of turbid media using a three-dimensional cross-correlation technique, in which for adjustment of the method a medium is placed in a test container (6) and illuminated by two parallel laser beams (B, C) that are inclined in such a way that their point of intersection is situated in the test container (6), and that detection optics (14a, 14b) are adjusted to this point of intersection so that the geometry of the detected scattered light is congruent with that of the laser beams (B, C), the scattered light being admitted by the detection optics (14a, 14b) and the amplitude of the cross-correlation functions being optimized by using a tiltable mirror (15), characterized in that first a laser beam (A) is directed so that it strikes the wall of the test container (6) perpendicularly and is reflected on this wall so that the reflected beam (A1) returns back into the incident laser beam (A), that the laser beam (A) is split into two parallel laser beams (B, C), and that these parallel laser beams (B, C) are inclined so that their point of intersection is situated in the test container (6), and that in a further step a mirror surface (87) passing through this point of intersection is provided in the test container (6), and that the intersecting laser beams (B, C) are thereby reflected, and that the reflected laser light is admitted by the detection optics (14a, 14b) situated on the detection side, and the mirror surface (87) is subsequently removed and a weakly scattering liquid is filled into the test container (6), and the amplitude of the cross-correlation functions is optimized.

2. Method according to claim 1, characterized in that in a further step of the method a cylindrical translucent container (85) filled with liquid is placed in such a way that the container surrounds the test container (6), and that the point of intersection of the laser beams (B, C) is then readjusted so that the point of intersection lies on the central axis (86) of the test container (6), and that the position of the detection optics (14a, 14b) is readjusted in such a way that the overlap volume is situated on the central axis (86) of the test container (6) and that the amplitude is then further optimized.

3. Method according to claim 2, characterized in that in this step of the method the cylindrical bath container (85) is filled with water and the test container (6) is filled with a turbid liquid.

4. Method according to claim 3, characterized in that the diameter of the cylindrical bath container (85) filled with liquid is such that the detection optics admit scattered light in the direction perpendicular to the longitudinal axis of the cylindrical bath which, observed from the side of the detection optics, comprises convergent or parallel beam bundles of the scattered light.

5. Method according to claim 1, characterized in that the laser beam (A) is positioned by means of tilting devices for the laser (2) and/or by means of mirrors.

6. Method according to claim 1, characterized in that the test container is a cuvette (6).

7. Method according to claim 1, characterized in that the detection optics are formed by glass fibers (14a, 14b) together with an integrated lens system.

8. Method according to claim 6, characterized in that, to position the laser beam (A) perpendicular to the cuvette wall, a dark liquid is placed in the cuvette, or that the cuvette (6) is mirror-coated.

9. Method according to claim 6, characterized in that the laser beams (B, C) intersect one another inside the cuvette (6).

10. Method according to claim 6, characterized in that the laser beams (B, C) intersect one another on the central axis (86) of the cuvette (6).

11. Method according to claim 6, characterized in that the mirror surface (87) is provided diagonally in the cuvette (6).

12. Method according to claim 11, characterized in that the mirror surface (87) is positioned in such a way that it extends through the central axis (86) of the cuvette fixture (5).

13. Method according to claim 6, characterized in that, to position the laser beam (A) perpendicular to the cuvette wall, the position of the laser beam (A) and of the beam (A1) reflected from the cuvette (6) are fixed by means of a glass plate placed in the beam path of same.

14. Method according to claim 6, characterized in that, for the adjustment of the point of intersection of the inclined parallel laser beams (B, C) on a longitudinal axis or the central axis (86) of the cuvette (6), a slightly turbid medium is placed in the cuvette.

15. Method according to claim 6, characterized in that the laser beam (A) is first split into two parallel laser beams (B, C), and that these laser beams (B, C) are then focused in the cuvette (6) by a lens (4).

16. Method according to claim 6, characterized in that the laser beam (A) is first focused by a lens and is then split into two laser beams (B, C) which are inclined in such a way that their point of intersection is situated inside the cuvette (6).

17. Method according to claim 6, characterized in that the laser beam (A) is split by a prism (74) into two laser beams (K, L), the point of intersection (M) of which is situated inside the cuvette (6).

18. Method according to claim 6, characterized in that the laser beam (A) is directed perpendicularly onto the vertical walls of the cuvette when a rectangular cuvette is used.

19. Device for suppressing multiple scattering during examinations of turbid media using a three-dimensional cross-correlation technique, in particular for carrying out the method according to one of the preceding claims, having an illumination side and a detection side situated on a base plate (1), whereby on the illumination side are situated a laser light source (2), an arrangement (3) for producing parallel laser beams, and a device (4) which inclines this arrangement, in addition to a test container (6) placed in a fixture (5) together with the medium to be examined, and whereby on the detection side are provided at least one tiltable mirror (15) and at least two detection optics (14a, 14b) situated in fixtures (13a, 13b) for admitting the scattered light and having at least two photon multipliers and one correlator for receiving cross-correlation or auto-correlation functions, characterized in that the arrangement for producing parallel laser beams forms one single unit and the device (4) which inclines the parallel laser beams is secured at the base plate (1) and that the detection optics (14a, 14b) and fixtures (13a, 13b) are fixable into a secure and stable position on a sub-structure plate (67) or on the base plate (1) thereby making the device portable.

20. Device according to claim 19, characterized in that the detection optics are formed by glass fibers (14a, 14b) together with an integrated lens system.

21. Device according to claim 19, characterized in that the arrangement for producing parallel beams is a beam splitter (3).

22. Device according to claim 21, characterized in that the beam splitter (4) is fixedly mounted in a positioning fixture (8) which is secured to the base plate (1).

23. Device according to claim 22, characterized in that the positioning fixture (8) is detachably secured to the base plate (1).

24. Device according to claim 21, characterized in that the beam splitter (3) is formed by a plane-parallel translucent plate (7) having a front side (7a) on which the incident laser beam is split in such a way that it exits at the back side of the plate (7) as two parallel beams, the front side (7a) of the plate (7) being fully mirror-coated in the region (22) situated outside the beam incidence, and the back side (7b) being semi transparently mirror-coated in the region (23) in which the transmitted beam (B) exits.

25. Device according to claim 24, characterized in that, in order to change the angle of incidence ($\ddot{y}$) of the beam about a tilting axis (P) which in the plane of extension of the plate (7) is parallel to the plane-parallel lateral surfaces (7a, 7b) of the plate (7) and which passes through the point of incidence (D) of the incident light beam (A), the plate (7) is tiltable.

26. Device according to claim 25, characterized in that the tilting axis (P) passes through the point of incidence (D) of the incident light beam (A), perpendicular to the plane of incidence of the beam.

27. Device according to claim 24, characterized in that the front side (7a) of the plate (7) is antireflectively coated in the region (21) of the beam incidence.

28. Device according to claim 24, characterized in that the back side (7b) of the plate (7) is antireflectively coated in the region (24) of emergence of the beam (C) which is reflected from the fully mirror-coated region (22) on the front side (7a).

29. Device according to claim 24, characterized in that, viewed perpendicular to the plate (7), an overlap region (27) is present in which the semi transparently mirror-coated region (23) on the back side (7b) overlaps with the fully mirror-coated region (22) on the front side (7a).

30. Device according to claim 24, characterized in that the overlap region is designed in such a way that the semi transparently mirror-coated region (32) on the back side (7b) of the plate (7) proceeds from a line (33) corresponding to the dividing line (34) between the fully mirror-coated region (30) and the region (29) of the incident beam or, respectively, the antireflectively coated region (29) on the front side (7a), and extends in the direction of the fully mirror-coated region (30) on the front side (7a) and meets a parallel line (34a) whose distance ($\ddot{y}d$) from the dividing line (34) is determined depending on the thickness (f) of the plate (7), the angle of incidence ($\ddot{y}$) of the beam, and the refractive index (n) of the plate material, and in order to change the angle of incidence ($\ddot{y}$) of the beam the plate (7) is tiltable about the tilting axis (35) and is displaceable along the tilting axis.

31. Device according to claim 29, characterized in that the semi transparently mirror-coated region (23) on the back side (7b) corresponds to the antireflectively coated region (21) on the front side (7a), and the fully mirror-coated region (22) on the front side (7a) corresponds to the antireflectively coated region (24) on the back side (7b), and in order to change the angle of incidence ($\ddot{y}$) of the beam the plate (7) is tiltable about the tilting axis (P), and is displaceable in a direction (R) perpendicular to the direction of the incident beam (A), in a plane perpendicular to the tilting axis (P), in such a way that the point of incidence of the light beam (A) and the tilting axis (P) corresponding to the change in the angle of incidence ($\ddot{y}$) of the beam may be separated at a distance from one another.

32. Device according to claim 29, characterized in that the semi transparently mirror-coated region (23) on the back side (7b) corresponds to the antireflectively coated region (21) on the front side (7a), and the fully mirror-coated region (22) on the front side (7a) corresponds to the antireflectively coated region (24) on the back side (7b), and in order to change the angle of incidence ($\ddot{y}g$) of the beam the plate (7) is tiltable about the tilting axis (P), and is displaceable in a direction (R) perpendicular to the tilting axis (P) and to the direction of the incident beam (A) in such a way that the point of incidence of the light beam (A) and the tilting axis (P) corresponding to the change in the angle of incidence ($\ddot{y}$) of the beam may be separated at a distance from one another.

33. Device according to claim 24, characterized in that the plate (7) is a glass plate.

34. Device according to claim 24, characterized in that the antireflectively coated, semi transparently mirror-coated, and fully mirror-coated regions of the plate (7) are prepared by coating the plate with aluminum or silver, or with a dielectric coating.

35. Device according to claim 19, characterized in that the plate is situated in the positioning fixture (8) at an angle of inclination of 45° with respect to the optical plane.

36. Device according to claim 19, characterized in that the beam splitter plate (7) situated in a socket lies with its entire surface in close contact with a surface (16) of the positioning fixture (8).

37. Device according to claim 36, characterized in that the surface (16) of the positioning fixture (8) is inclined at a fixed angle with respect to the optical plane, which is specified for the analyses.

38. Device according to claim 19, characterized in that a glass prism (74) is provided as the beam splitter which splits the laser beam (A) into two partial beams (K, L), which are inclined in such a way that they intersect inside the cuvette (6).

39. Device according to claim 22, characterized in that the cuvette fixture (8) is constructed in two parts, and that the inner wall of the external fixture and the outer wall of the internal fixture have a conical design.

40. Device according to claim 22, characterized in that the cuvette fixture (8) may be temperature-controlled and insulated.

41. Device according to claim 22, characterized in that the cuvette fixture has a continuously adjustable x-y displacement device (77, 78).

42. Device according to claim 22, characterized in that the cuvette fixture has a plurality of openings for the laser light which is transmitted at various angles.

43. Device according to claim 19, characterized in that the glass fiber fixtures (13a, 13b) may be adjusted manually or by motor control.

44. Device according to claim 19, characterized in that a system comprising mirrors (15, 15b) and glass fibers (14a, 14b, 14c) is provided on the detection side for the detection of scattered light which is transmitted at various angles and that the position of the individual mirrors and glass fibers is variably adjustable and firmly fixable on a substructure plate (67) which is connected to the base plate (1).

45. Portable device for carrying out examinations of turbid media using a three-dimensional cross-correlation technique and for suppressing the influence of multiple scattering, using a base plate (1) upon which an adjustable laser (2) is positioned in tilting devices or by means of mirrors for directing the laser beam perpendicularly onto the wall of a cuvette (6) filled with a medium to be examined, and having a translucent plate (7) which in some sections is completely mirror-coated and in other sections is semi transparently mirror-coated and which serves as a beam splitter (3), the plate being firmly secured to the base plate (1) using a positioning fixture (8) whose support surface (16) for the translucent plate (7) is situated at a fixed angle with respect to the base plate (1), and the positioning fixture (8) is detachably secured to the base plate (1) and to a cuvette fixture having receptacles for the cuvette (6) and for a cylindrical translucent container (70) filled with a liquid which is situated on the base plate (1), and having displacement devices which allow the cuvette fixture (5) to be continuously positioned, the cuvettes (6) being used having mirror surfaces (87) provided therein, and tilting and displacement devices for at least two detection optics (14a, 14b) being situated so that they can be fixedly positioned on a base plate (1a) on the detection side of the device and so that this base plate (1a) can be firmly locked on the base plate (1), and in addition a photon multiplier and correlators for receiving cross-correlation or auto-correlation functions are provided.

46. Device for suppressing multiple scattering during examinations of turbid media using a three-dimensional cross-correlation technique, having an illumination side on which side a laser source can be situated, a detection side on which side the turbid media can be positioned, an arrangement (3) for producing parallel laser beams, and a device (4) which inclines the parallel laser beams, wherein the beam-producing arrangement comprises a beam splitter plate which splits beam A from the laser source into two parallel beams B and C substantially simultaneously with inclining beams B and C, and wherein beams B and C are focused to overlap at the turbid media.

* * * * *